United States Patent [19]

Cho

[11] Patent Number: 6,136,599
[45] Date of Patent: Oct. 24, 2000

[54] HUMAN HYBRID HOST CELL FOR MAMMALIAN GENE EXPRESSION

[75] Inventor: Myung-Sam Cho, Pinole, Calif.

[73] Assignee: Bayer Corporation, Berkeley, Calif.

[21] Appl. No.: 09/209,920

[22] Filed: Dec. 10, 1998

[51] Int. Cl.[7] .............................. C12N 5/02; C12N 5/06
[52] U.S. Cl. ..................... 435/325; 435/326; 435/335; 435/346
[58] Field of Search .................................... 435/440, 325, 435/326, 335, 346

[56] References Cited

FOREIGN PATENT DOCUMENTS 2085887  5/1982  United Kingdom .

OTHER PUBLICATIONS

Stillman, et al. (Molec. & Cell. Biol., 1985; 2051–2060).
Peshwa, et al. (Biotech. & Bioeng., 1993; 179–187).
Walls, et al. (Gene, 1989; 139–149).
ATCC Cell Lines and Hybridomas (8th Ed., 1994; 149).

Primary Examiner—Christina Y. Chan
Assistant Examiner—Marianne DiBrino
Attorney, Agent, or Firm—Michael J. Beck; James A. Giblin

[57] ABSTRACT

Human/human hybrid cells were made via fusion of human embryonic kidney cells (293S) and modified Burkitt's lymphoma cells (2B8). The fusion cells are useful as host cells for the recombinant expression of mammalian genes. The advantages of using these hybrid clones of human kidney- and B-cells, called HKBs, for mammalian gene expression, include (i) the cells are negative for immunoglobulin expression, (ii) the cells grow easily in plasma protein-free medium (with or without the addition of recombinant insulin) as suspension cultures in a shake flask or in a fermenter (iii) the cells are very susceptible for transfection of DNA, and (iv) the cells secrete high levels of heterologous recombinant proteins, such as recombinant monoclonal antibodies, soluble ICAM-1, rIL-4, and rFVIII.

22 Claims, 3 Drawing Sheets

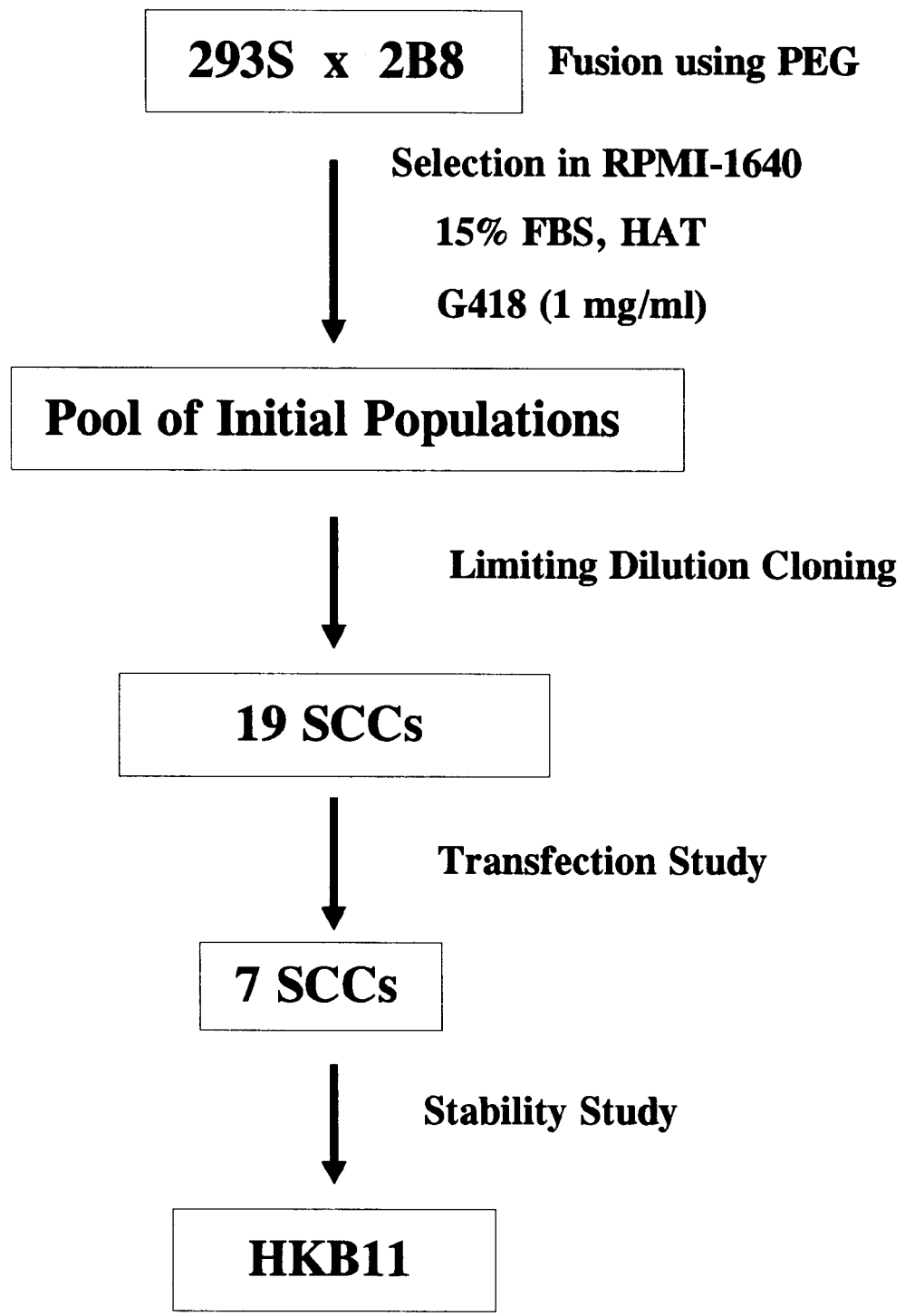
Fig._1

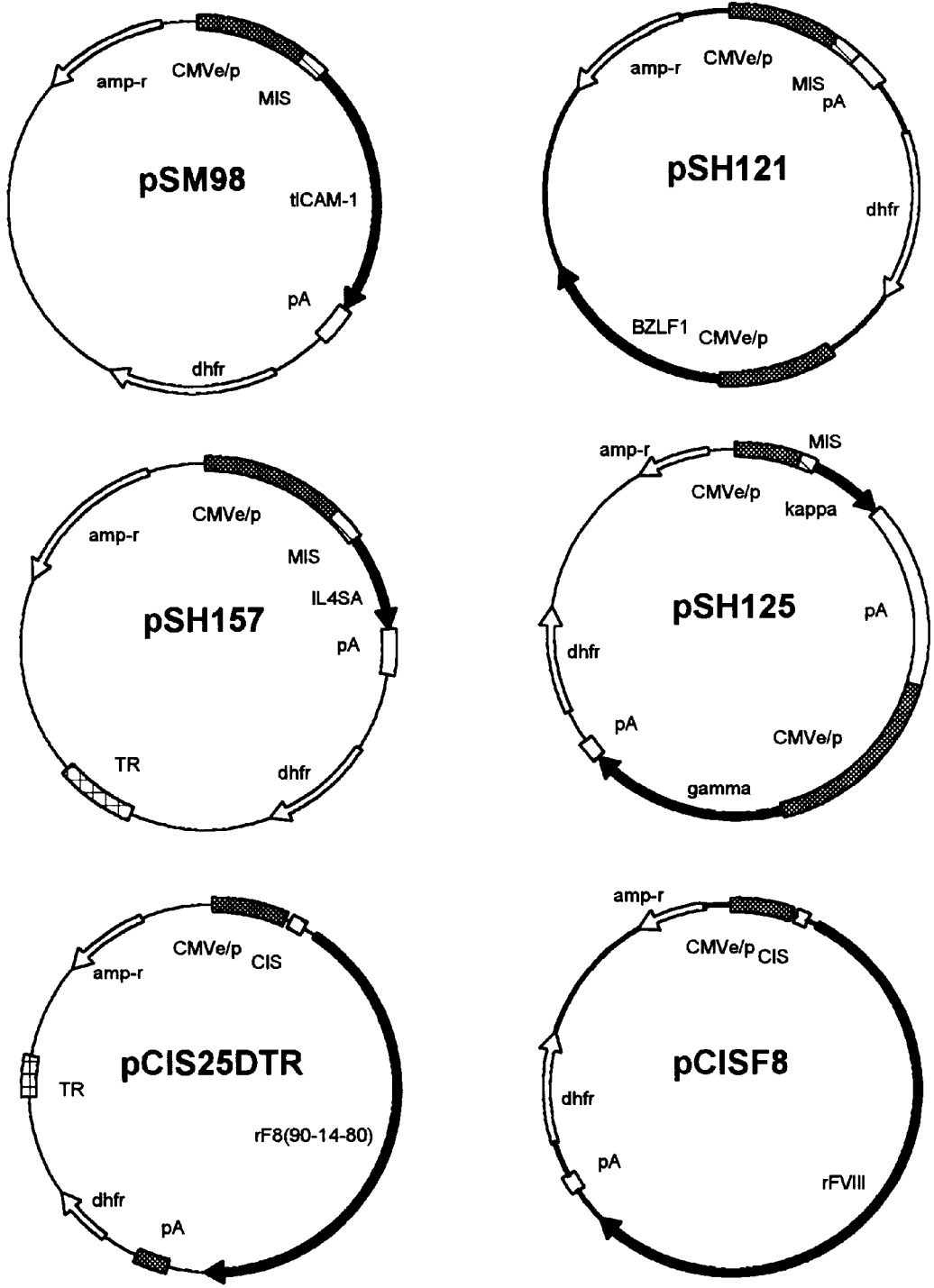
Fig._2

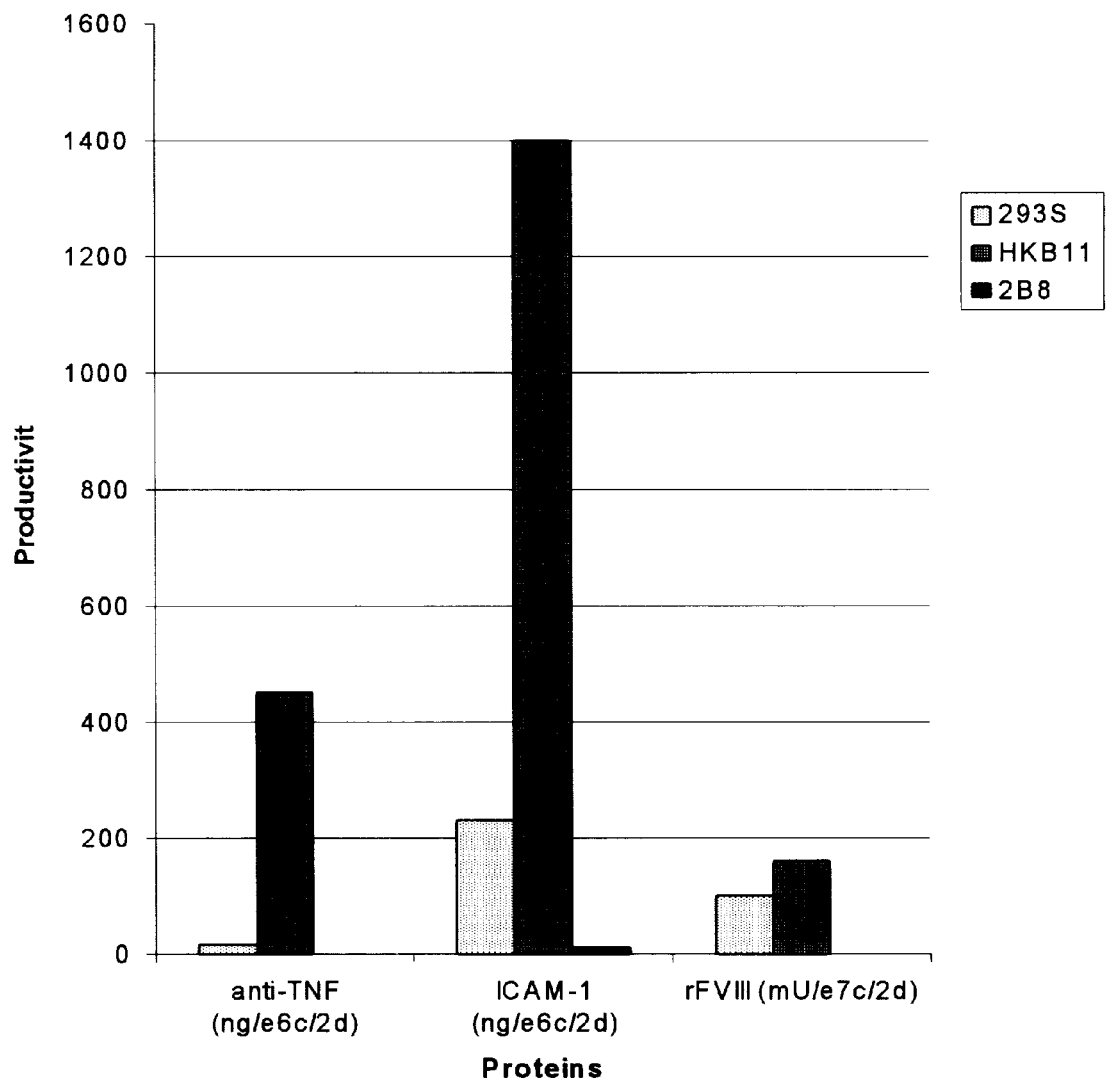
Fig._3

HUMAN HYBRID HOST CELL FOR MAMMALIAN GENE EXPRESSION

RELATED APPLICATIONS

The application to Cho and Chan Ser. No. 09/209,915, "Terminal repeat sequence of Epstein-Barr virus enhances drug selection ratio," and the application to Cho et al. Ser. No. 09/209,916, "Expression system for factor VIII," contain related subject matter. Both applications were filed on the same day as the current application.

BACKGROUND OF INVENTION

1. Field

This invention relates generally to the genetically engineered mammalian cell lines for the production of biologically active protein. Specifically, the invention is concerned with human hybrid cell clones derived from the fusion process of human embryonic kidney (293S) cells and Burkitt's lymphoma cells. These human hybrid cells can be used for the production of heterologous proteins.

2. Background

To date, most therapeutic recombinant proteins have been produced from non-human mammalian cells. Some examples are:

Chinese hamster ovary (CHO) (dhfr-) cells (Urlaub et al., 1980, Proc Natl Acad Sci U.S.A. 77: 4216–4220) with the amplifiable selection marker dihydrofolate reductase (Kaufman et al., 1982, Mol. Biol. 159: 601–621; Gasser et al., 1982, Proc Natl Acad Sci U.S.A. 79: 6522–6526) have been used for the production of therapeutic recombinant protein.

A variety of recombinant therapeutic proteins are known to be produced in mammalian cells, e.g. recombinant factor VIII (rFVIII) (Kaufman et al., 1988, J Biol Chem 263: 6352–6362), tissue plasminogen activator (tPA) (U.S. Pat. No. 4,766,075 to Goeddel et al., 1988), erythropoietin (EPO) (U.S. Pat. No. 4,703,008 to Lin, 1987), and monoclonal antibodies (mAbs) (U.S. Pat. No. 4,816,397 to Boss et al., 1989).

Baby hamster kidney (BHK) cells (BHK21) were used for production of rFVIII after G418 selection and methotrexate (MTX) amplification of G418 resistant cells (U.S. Pat. No. 4,965,199 to Capon et al., 1990).

Mouse myeloma (NS0) cells were used for production of engineered human anti-TNF antibody (EHAT). (U.S. Pat. No. 4,816,397 to Boss et al., 1989). However, this cell line produces proteins having mouse specific carbohydrate patterns which are not favored for human use.

A human cell line, Namalwa (of Burkitt's lymphoma origin), was used for production of alpha-interferon by Wellcome Research Laboratory and for the production of pro-urokinase (Satoh et al., 1996, Cytotechnology 18: 167–185, 1996), tissue-plasminogen activator (t-PA) (Khan et al., 1995, Biochem Soc Trans 23: S99), granulocyte-macrophage colony-stimulating factor (Okamoto et al., 1991, Arch Biochem Biophys 286: 562–568), interferons and lymphotoxin (Hosoi et al., 1991, Cytotechnology 5: 17–34), and granulocyte colony stimulating factor (Hosoi et al., 1991, Cytotechnology 7: 25–32) by Tokyo Research Laboratories. However, these cells were very difficult to transfect with DNA.

Walls et al. (1989, Gene 81: 139–149) have reported on the use of the dhfr/MTX co-amplification strategy to express functional protein C in human embryonic kidney cells (293S cells). 293 cells (Stillman et al., 1985, Mol. Cell. Biol. 5: 2051–2060) are known as making large aggregates in suspension, especially under high calcium concentration (>100 μM), which promotes larger aggregation and lower cell viability (Peshwa et al., 1993, Biotech and Bioeng 41: 179–187). All references cited are herein incorporated by reference.

SUMMARY OF INVENTION

Clones of hybridized human cells have now been established which are easily transfected by electroporation or cationic liposome and which are easily adapted to growth in suspension culture. Heterologous proteins can be expressed using low levels (50–100 nM) of MTX amplification in a human cell environment. In addition, the cells are easily adapted to growth in serum-free medium.

These cells are the product of a fusion between human embryonic kidney (293S) cells and Burkitt's lymphoma cells. See FIG. 1 for the summary. These hybrid clones, called HKBs, harbor a defective EBV-genome derived from HH514-16, which is a cell line originating from Burkitt's lymphoma cells, P3HR1 (Hinuma et al., 1967, J Virol 1: 1045–1051). P3HR1 cells harbor non-immortalizing EBV. HH514-16 is a clone of P3HR1 (Hinuma et al., 1967, J Virol 1: 1045–1051) which harbors non-immortalizing EBV. HH514-16 has lost a het-DNA, a latency-interrupting DNA, during the cloning process (Rabson et al., 1983, Proc Natl Acad Sci U.S.A. 87: 3660–3664). Therefore, EBV of HKB clones is non-immortalizing virus and stays as a latency.

HKBs are human hybrid host cells suitable for the recombinant production of therapeutic proteins. These host cells are obtained by the hybridization of different parent cell lines, each having different advantageous characteristics. Host cells which possess advantageous characteristics of each of the parent cell lines are obtained from the cells resulting from the hybridization.

The host cells may be genetically engineered to express high levels of a wide range of proteins. Proteins which may be produced by the engineered host cells include, but are not limited to, soluble ICAM-1, recombinant interleukin-4 (IL-4), rFVIII, BDD-FVIII B domain deleted factor VII, (as disclosed in the related application to Cho et al. Ser. No. 09/209,916, incorporated herein by reference), tPA, and EPO, and derivatives of these proteins. It has also been found that, although endogenous immunoglobulin (Ig) was not expressed, recombinant Ig expression from the engineered host cells was was high. Proteins produced from HKB11 cells have human specific glycosylation profile. Therefore, the clones are optimal host cells for the production of gene-engineered Ig and other proteins.

As used herein, a cell of Burkitt's lymphoma origin is a cell that is a Burkitt's lymphoma cell, derived from a Burkitt's lymphoma cell, derived from another cell of Burkitt's lymphoma origin, or a cell resulting from mitotic division of any of the above. "Derived from" in this context is intended to include, but not be limited to, normal mitotic cell division and processes such as transfections, cell fusions, or other genetic engineering or cell biology techniques used to alter cells or produce cells with new properties. Similarly, a cell of human embryonic kidney origin is a cell that is a human embryonic kidney cell, derived from a human embryonic kidney cell, derived from another cell of human embryonic kidney origin, or a cell resulting from the mitotic division of any of the above. Also, a cell of 293S origin is a cell that is a 293S cell, derived from a 293S cell, derived from another cell of 293S origin, or a cell resulting from the mitotic division of any of the above. A heterologous protein is a protein that a cell has been engineered to produce.

BRIEF DESCRIPTION OF THE FIGURES

FIG. 1 shows a summary of the derivation of the HKB cells.

FIG. 2 shows physical maps of expression vectors mentioned in the text. All plasmids are constructed based on a pBR322 backbone and contain a dhfr expression unit. All genes coding proteins of interest are under the regulation of CMV enhancer/promoter (CMVe/p); 5'intron (MIS or CIS) was positioned at the 5'end of the genes, except BZLF1. Poly A signal region was indicated as pA. Both plasmids, pSH157 and pCIS25DTR, contain a sequence of EBV-TR (402 bp).

FIG. 3 shows a comparison of host cell lines for gene expression in transient transfection assay. Transfections were performed under the same conditions: the same number of cells of 293S, 2B8, and HKB11 were transfected with the same amount of plasmid DNAs using the same transfection agent. Tissue culture fluids were harvested at 2 days after transfection. Protein production levels were determined by ELISA (IgG and ICAM-1; measured as ng protein/$10^6$ cells/2 days) and by Coatest® assay kit (rFVIII; measured as milliunits/$10^7$ cells/2 days).

SPECIFIC EMBODIMENTS

Materials and Methods

HH514–16 was kindly provided by Dr. George Miller (Yale University). 293S cells were obtained from Dr. Brad Zerler (Molecular Therapeutic Institute, West Haven, Conn.) 293S cells are 293 cells (ATCC CRL-1573) which have been adapted to grow in suspension culture (Stillman et al., 1985, Mol Cell Biol 5: 2051–2060).

Plasmids

All expression vectors used in this report were basically pBR322-based plasmid with function dhfr gene expression segement. Physical maps of expression vectors are described in FIG. 2. Plasmids, pSH157 and pCIS25DTR, have also terminal repeat sequence of Epstein-Barr virus (EBV-TR). See patent application to Cho and Chan designated MSB-7254, "Terminal repeat sequence of Epstein-Barr virus enhances drug selection ratio," for the EBV-TR sequence. The vector pSH13 1, which has been deposited with the American Type Culture Collection, ATCC 98879, may be used to generate expression vectors for a chosen protein as described in Cho and Chan (MSB-7254, supra.)

ELISA

To measure tICAM-1 secretion, a monoclonal antibody to ICAM-1, C92.5 (McClelland et al., 1991, Proc Natl Acad Sci U.S.A. 88: 7993–7997) was adsorbed onto round bottom microtiter plates. The plates were blocked by treatment with a solution of phosphate buffered saline (PBS) containing 1% bovine serum albumin (BSA), then incubated with tICAM-1 containing samples. Plates were then washed with washing buffer (PBS plus 0.005% Tween 20) and incubated with biotinylated C78.5, a second monoclonal antibody to a different epitope on tICAM-1 (McClelland et al., 1991, supra). After washing, the plates were incubated with HRP-streptavidin. The plates were then washed with washing buffer, reacted with tetramethyl benzidine (TMB), and the reaction was stopped with 1 N HCl. The tICAM-1 concentration was determined by reading the OD at 450/570 nm and comparing to a standard curve of purified tICAM-1.

To measure immunoglobulin (Ig) secretion, anti-Ig antibody was used to coat the plate and biotinylated anti-Ig antibody was used as a detection antibody. A known concentration of Ig molecule was used as a standard. Otherwise, the process remained the same.

To measure interleukin-4 (IL-4) secretion, anti-IL-4 antibody was used to coat the plate, and biotinylated anti-IL-4 antibody was used as a detection antibody. A purified IL-4 molecule was used as a standard.

Assay for Measuring rFVIII Secretion

The rFVIII molecule was quantitated with reagents from the Coatest® VIII:C/4 Kit (Chromogenix, Mölndal, Sweden). A U.S. standard anti-hemophilic factor (factor VIII) known as MEGA 1 (Office of Biologics Research and Review, Bethesda, Md.) was used as the standard of measurement to EIA/RIA A/2 plates (Corning, Corning, N.Y.) pre-warmed to 37° C. on Select Heat Blocks (VWR Scientific, San Francisco, Calif.). Factor IXa, factor X, phospholipid and $CaCl_2$ were added to each sample and incubated for 10 minutes for the activation of factor X. A chromogenic substrate (S2222) was then added and incubated for 10 minutes to liberate the chromogenic group, pNA. This reaction was stopped by the addition of 50% acetic acid. The colorimetric absorbance was then measured at 405/450 nm on a SPECTRAmax® 250 spectrophotometer microplate reader (Molecular Devices, Sunnyvale, Calif.) and the data was calculated via a SOFTmax® PRO software provided by Molecular Devices.

Derivation of HAT-Sensitive and G418-Resistant Burkitt's Lymphoma Cell Line

To obtain HAT-sensitive cells, hypoxanthine-guanine phosphoribosyl transferase (HGPRT)-deficient cell lines (Szybalska et al., Proc. Natl. Acad. Sci. U.S.A. 48: 2026–2034, 1962; Littlefield, Proc. Natl. Acad. Sci. U.S.A. 50: 568–576, 1963) were established by the standard protocol described by Siadak et al. (U.S. Pat. No. 4,834,975, 1989).

HH514-16 cells (obtained from Dr. G. Miller, Yale University), which are free of EBV het-DNA (Rabson et al., 1983, Proc Natl Acad Sci U.S.A. 87: 3660–3664), were treated with 300 µg/ml of methanesulfonic acid ethyl ester (MSE) (Sigma, St. Louis, Mo.) in RPMI-1640 suspension medium (Life Science, Gaithersburg, Md.) supplemented with 15% fetal bovine serum (FBS) (Hyclone, Logan, Utah) for 24 hours. After washing the cells with medium, cells were plated in medium containing 6-thioguanine (6TG) (Sigma) (5 µg/ml) to select for HGPRT-negative cells. The concentration of 6TG was increased from 5 µg/ml to 30 µg/ml during the six month selection period. The cells were then tested for their sensitivity to HAT-containing medium. Single cell clones (SCCs) were obtained from limiting dilution cloning (one cell per well in 96-well plates) of HAT-sensitive population A5. One of the SCCs, A5/ID7, was transfected with pSV2neo, which has neo gene under SV40 promoter in pBR vector, to obtain G418-resistant cells. One of the G418 (1.5 mg/ml) resistant SCCs, referred to as 2B8 (deposited with the American Type Culture Collection, 10801 University Blvd., Manassas, Va. 20110, on Sep. 16, 1999 and granted accession No. CRL-12569), was used for fusion.

EXAMPLE 1

Cell Fusion and Derivation of Single Cell Clones

Cell fusion was primarily performed according to the polyethylene glycol (PEG) fusion method described by Kennett (1979, Meth Enzymol 58: 5–359). Five million each of 293S and 2B8 cells in logarithmic growth were washed with PBS without $Ca^{++}$ and $Mg^{++}$ (Life Technologies, Rockville, Md.) and seeded onto one well of a 6-well plate pre-treated with peanut agglutinin (Sigma) (5 µg/ml). The 6-well plates loaded with cells were centrifuged at 400 g for 6 minutes in a Beckman J-6M/E centrifuge (Beckman, Palo Alto, Calif.). After removing the PBS from the well, cells were treated with 2 ml of 40% (w/v) PEG (Sigma) for one minute. As a control, one well was not treated with PEG.

Cells were washed three times with 5 ml PBS containing 5% DMSO followed by three PBS washes. Cells were incubated with fresh medium supplemented with 15% FBS for 25 minutes. Cells were seeded onto 96-well plates ($1.2 \times 10^6$ cells per plate) using the fresh medium containing G418 (1 mg/ml) and HAT (Life Technology) supplemented with 15% FBS. The cells were fed twice a week using the selection medium. In this example, for the initial selection, the 293S cells had the desirable characteristic of lacking sensitivity to the HAT containing medium, and, similarly, the 2B8 cells had the desirable characteristic of being resistant to G418.

While the fused cells grew under selective conditions, the mixed cells did not grow under the same conditions. Three weeks after selection, the initial populations were transferred to larger formats. To obtain SCCs, the stably growing twenty initial populations were mixed and subjected to limiting dilution cloning (one cell per well) using the selective medium. Nineteen SCCs were selected from 15×96-well plates after careful monitoring the individual clones using a microscope. The SCCs derived from the fusion experiment were referred to as HKB cells (Hybrid cells of human kidney- and B-cells). Seven SCCs were chosen from the transfection study. These seven SCCs were further tested for the stable production of various proteins. One of the seven SCCs, HKB11, (deposited on Sep. 16, 1998 with American Type Culture Collection, 10801 University Blvd., Manassas, Va. 20110, and granted accession number CRL-12568) was chosen as a preferred mammalian cell host for the production of heterologous proteins. See FIG. 1 for the summary.

EXAMPLE 2
Characterization of the HKB Clones

Although all hybrid cells were selected under selective conditions, the hybrid status was confirmed by counting the chromosome numbers in cells. Indeed, all of the HKBs showed a modal chromosome number of 90-110. These numbers were similar with the sum of modal chromosome numbers of 293S and 2B8 (64 and 47, respectively, according to ATCC data). 293S (Stillman et al., 1985, Mol Cell Biol 5: 2051-2060) is suspension adapted 293 (ATCC CRL-1573).

All hybrid cell clones were tested for endogenous Ig (mu and kappa) expression by direct immunofluorescence assay using methanol fixed cells to determine which cell clones secrete endogenous Ig. In repeated experiments over a longer period, these cells were observed to be negative for mu- and kappa-chains expression based on immunofluorescence test (Table 1) and ELISA (data not shown).

TABLE 1

Detection of Ig-gene expression.

| Cells | Heavy chian (mu) | Light chain (kappa) |
|---|---|---|
| | Gene expression | |
| 293S | negative | negative |
| 2B8 | positive | positive |
| HKB | negative | negative |

Table 1 shows the results observed from the immunofluorescence testing of three types of cells. Cells were resuspended in PBS and applied as a smear on a glass slide. After drying the cells, the slides were fixed in a cold (-20° C.) methanol for 5 minutes. The cells were stained with FITC-anti human kappa and anti human mu chains (1:20 dilution) (Zymed Laboratories, Inc., So. San Francisco, Calif.) in a humidified chamber at 37° C. for 45 minutes. After rinsing slides with PBS for 10 minutes, slides were mounted with cover glass using PBS/Glycerol (1:1). Cells were observed in a fluorescence microscope (Carl Zeiss, Inc., Thornwood, N.Y.).

The human specific pattern of sialic acid linkage, alpha (2-6) sialyltransferase was confirmed by a FACS analysis of the HKB cells using FITC conjugated *Sambucus nigra* lectin (SNA) (Sigma, St. Louis, Mo.) Protein secreted from the HKB cells (clone 1G2) showed alpha(2-3) and alpha(2-6) linkage of sialic acid of glycosylation profile analyzed by oligosaccharide fingerprinting method (data not shown). This observation indicates that HKB cells derived from fusion of 293S and 2B8 cells maintained human specific glycosylation enzymes.

To test if these hybrid cells have the capacity to express foreign genes, the cells were transfected with expression vectors for ICAM-1 and IgG (anti-TNF antibody). To test secretion of IgG, HKB cells ($5 \times 10^6$ cells) were transfected by electroporation with 10 μg of plasmid DNA providing for functional expression of heavy (gamma) and light (kappa) chains. To test secretion levels of soluble ICAM-1, HKB cells ($5 \times 10^6$ cells) were transfected by electroporation with 10 μg of plasmid DNA providing for functional expression of soluble ICAM-1. Secretion levels were determined by an ELISA for IgG or ICAM-1. All 19 SCCs secreted relatively high levels of ICAM-1 (100–500 ng/ml/2d) and IgG (30–200 ng/ml/2d) in a transient transfection assay (Table 2). These data indicate that the hybrid cells support the expression of transfected Ig genes, although endogenous Ig gene expression was extinguished.

TABLE 2

Transient transfection assays for the secretion of IgG and soluble ICAM from HKB clones which are obtained early after cloning process. Values are secretion levels of protein (ng/ml/2d).

| HKB clone | IgG | Soluble ICAM-1 |
|---|---|---|
| 1 | ~150 | ~500 |
| 2 | ~30 | ~30 |
| 3 | ~20 | ~50 |
| 4 | ~80 | ~200 |
| 5 | ~100 | ~500 |
| 6 | ~50 | ~300 |
| 7 | ~40 | ~200 |
| 8 | ~30 | nd |
| 9 | ~80 | nd |
| 10 | ~80 | ~100 |
| 11 | ~200 | nd |
| 12 | ~100 | nd |
| 13 | ~80 | ~150 |
| 14 | ~80 | nd |
| 15 | ~30 | ~200 |
| 16 | ~80 | ~200 |
| 17 | ~160 | ~500 |
| 18 | ~80 | ~200 |
| 19 | ~80 | ~100 | nd = not done

Epstein Barr virus (EBV) exists as episomes in 2B8 cells. All the SCCS were positive for EBNA-1 expression (data not shown), which indicates that they are positive for EBV. However, it was not known whether a complete EBV genome still existed in the hybrid cells. Therefore, the status of the EBV genome in the hybrid cells was tested by transfecting the cells with the EBV genome fragment BZLF1, a latency interrupting trans-activating gene. HKB cells ($5 \times 10^6$ cells) were transfected with 10 μG of plasmid DNA (pSH121) allowing functional expression of BZLF1. Detection of EBV capsid antigen (EBV-VCA) was performed by indirect immunofluorescence using human serum containing anti EBV-VCA titer and FITC conjugated anti-human IgG. Technical details of the immunofluorescence test is described above. As shown in Table 3, mock transfected cells were negative for expression of EBV capsid antigen (EBV-VCA), which indicated that they were negative for EBV replication. However, a small percentage of the transfected cells were positive for the antigen expression. These data indicate that the hybrid cells harbor EBV genome in its latent form.

TABLE 3

Induction of EBV replication by transfection with BZLF1.

| | Expression of virus capsid antigen (%) | |
|---|---|---|
| HKB clone | mock transfection | BZLF1 |
| HKB1 | Negative | 0.20% |
| HKB5 | Negative | 1–2% |
| HKB7 | Negative | 0.20% |
| HKB11 | Negative | 0.20% |
| HKB13 | Negative | 0.50% |
| HKB17 | Negative | 0.20% |
| HKB19 | Negative | 1–2% |

The hybrid cells were adapted to serum-free medium by serial two fold reduction of FBS in shake flasks. After two weeks, cells were growing in the medium without FBS. The cells grew as small aggregates in shake flasks. In contrast to 293S cells, the hybrid cells were easily adaptable to serum-free suspension cultures. Hybrid cells in serum-free and albumin-free medium supplemented with transferrin and insulin could be maintained for more than one year in suspension culture using shake flasks.

To compare secretion levels of transfected gene products, one of the clones, HKB11, and parental cells, 293S and 2B8, were transfected with pSM98 (soluble ICAM-1), pSH125 (anti-TNF IgG), and pCISF8 (rFVIII). As shown in FIG. 3, secretion levels of ICAM-1 and IgG were much higher (approximately 10-fold) in HKB11 cells than 293S cells. Secretion levels of both proteins from 2B8 were undetectable. Secretion levels of rFVIII in HKB11 cells was similar to that of 293S cells. These data indicate that transfection efficiency of HKB11 cells are much better than parental cells.

EXAMPLE 3
Derivation of Stable HKB Clones Secreting Heterologous Proteins

Hybrid clones were tested for the stable expression of proteins in a gene amplifiable system (dhfr/MTX). Cells were first transfected with an appropriate expression vector, and then the transfected cells (usually $10^6$ cells per 96-well plate) were seeded and selected/amplified with the selection medium lacking hypoxanthine and thymidine, but supplemented with FBS and MTX (50 nM). After the first screening of the plates, the cells from the high secreting wells were chosen and transferred to the 6-well plates. The cells in the 6-well plates were further amplified with increasing concentrations of MTX (100, 200, and 400 nM) in medium. The initial populations of the 6-well plates were further screened for deriving the best population. Eventually, these populations were used for cloning of single cell derived clones. As shown in table 4, HKB11 cells were optimal for producing high levels of heterologous human proteins. For the production of ICAM-1, Ig, and an IL-4 derivative, HKB11 cells were as good as CHO cells (data are not shown). However, HKB clones grew faster than CHO clones and could be adapted easily to suspension culture and to serum-free conditions. In case of BDD-FVIII production, HKB11 clones showed about tenfold greater productivity than CHO clones. The above results indicate that HKB11 cells are an optimal human cell host useful for the expression of human therapeutic proteins.

TABLE 4

Heterologous protein production from HKB clones.

| Protein | Cell host | MTX amplification | Specific Productivity |
|---|---|---|---|
| ICAM-1 | HKB11 | 100 nM | 10 pg/c/d[1] |
| Ig | HKB13 | 50 nM | 12 pg/c/d |
| BDD-FVIII | HKB11 | 400 nM | 5–10 uU/c/d[2] |
| IL-4SA | HKB11 | 100 nM | 5 pg/c/d[3] |

[1]ICAM-1 production level from HKB clones were similar with that from 293S cells. HKB clone secreting ICAM-1 was easily adaptable to suspension culture, while 293S clones were very difficult to adapt to suspension culture.
[2]The secretion level of BDD-FVIII secretion was about 10 times higher than those from the clones derived from CHO cells transfected with the same expression vector.
[3]Gram quantity of IL-4SA(T13D/R121E) production was possible 6 months post transfection using HKB11, while it took a few months longer using CHO cells in simultaneous experiments using the same expression vector and similar process.

The cell lines derived by the above process included (i) soluble ICAM-1 secreting clones (10 pg/cell/day) derived from HKB11 cells transfected with pSM98 after amplification in 100 nM MTX, (ii) monoclonal antibody (anti-TNF) secreting single cell clones (12 pg/cell/day) derived from the HKB13 transfected with pSS125 after amplification in 50 nM MTX and limiting dilution cloning without MTX, (iii) truncated rFVIII (BDD-FVIII) secreting single cell clones (5–10 $\mu$U/c/d, in serum-free condition) derived from HKB11 cells transfected with pCIS25DTR after amplification (400 nM MTX) and limiting dilution cloning without MTX, and (iv) IL-4 derivative (IL-4 selective agonist, IL-4SA; mutated two positions of amino acid, T13D and R121E) secreting clones (5 pg/c/d) derived from HKB11 transfected with pSH157 after MTX amplification. The IL-4SA secreting HKB clone, 1G2, (deposited on May 19, 1999 with American Type Culture Collection, 10801 University Blvd., Manassas, Va. 20110, and granted accession number PTA-87) was used for relatively quick production of small amounts of protein (gram quantity). See FIG. 2 for the physical map of the expression vectors mentioned above.

DISCUSSION

The hybrid human cell lines described herein display desirable characteristics possessed by their parent cell lines. HKB cell lines, which are produced by the fusion of human embryonic kidney cells (or cells derived from human embryonic kidney cells) with Burkitt's lymphoma cells (or cells derived from Burkitt's lymphoma cells), are useful for developing cell lines for the expression of heterologous proteins.

The initial purpose of establishing the hybrid cell lines of 293S and 2B8 was to resolve the aggregation problem of 293S cells, which tend to clump when grown in suspension culture (an undesirable characteristic). The HKB cells that were developed from the hybridization process grow as a monolayer when cultured in T-flasks. However, these cells grow as suspension cells (do not form large aggregates) when they are cultured in suspension mode. HKB cells are very easy to handle for transfection, and transfection efficiency is much higher than with 293S cells.

Although the transformation or hybridization event required in most cases to produce a stable cell line may result in altered glycosylation profiles (Yamashita, 1989, J Biol Chem 264: 2415–2423), it was found that HKB11, which is a somatic hybrid cell line, has typical human glycosylation enzymes, e.g. alpha(2-3) and alpha(2-6) sialyl transferases. Moreover, proteins produced from transfected HKB cells have normal human glycosylation patterns of alpha(2-3) and alpha(2-6) sialic acid linkages.

In summary, HKBs are hybrid human cells having desirable characteristics from each of the parental cell lines; namely, growing easily in suspension culture without aggregation (as observed with 2B8 cells) and ease of transfection and desirable secretion characteristics (as observed with 293S cells). The preferred hybrid human cell line, HKB11, is negative for immunoglobulin gene expression as are 293S cells. This trait is advantageous in cases where it is desired to recombinantly produce monoclonal antibodies from human cells. The discovery that fusion of human cells has resulted in cells having advantageous characteristics serves to encourages further fusion studies using 293S and other cell lines of B-cell origin, e.g. Namalwa and 6F11, to obtain new combinations of traits in the hybrid cells from fusing different parental cell lines.

The above examples are intended to illustrate the invention and it is thought variations will occur to those skilled in the art. Accordingly, it is intended that the scope of the invention should be limited only by the claims below.

What is claimed is:

1. A cell derived from the fusion of a cell of human embryonic kidney origin with a 2B8 cell (ATCC deposit number CRL-12569).

2. A cell according to claim 1 wherein the cell of human embryonic kidney origin is a 293 cell.

3. A cell according to claim 1 wherein the cell of human embryonic kidney origin is a 293S cell.

4. A cell according to claim 1 which expresses a heterologous protein.

5. A cell according to claim 4, wherein the heterologous protein is selected from the group consisting of FVIII, BDD-FVIII, monoclonal antibody, anti-TNF antibody, rIL4, tPA, and EPO.

6. A cell line designated HKB11 (ATCC deposit number: CRL-12568).

7. An HKB11 cell line which has been engineered to express a heterologous protein.

8. A cell line according to claim 7 wherein the protein is ICAM-1.

9. A cell line according to claim 7 wherein the protein is BDD-FVIII.

10. A cell line according to claim 7 wherein the protein is a monoclonal antibody.

11. A cell line according to claim 10 wherein the monoclonal antibody is anti-TNF.

12. A cell line according to claim 7 wherein the protein is rIL4.

13. A cell line according to claim 7 wherein the protein is FVIII.

14. A cell line according to claim 7 wherein the protein is tPA.

15. A cell line according to claim 7 wherein the protein is EPO.

16. A cell line according to claim 7 wherein the protein is IL-4SA (T13D/R121E).

17. A cell line according to claim 7 wherein the protein is a human protein having a human glycosylation profile.

18. A method of producing hybrid human cells useful for expression of a heterologous protein comprising the steps of a) obtaining cells of human embryonic kidney origin, b) obtaining 2B8 cells (ATCC deposit number CRTL-12569), c) contacting the cells of step a) with the cells of step b) under conditions which allow cell fusion to occur, d) screening the cells resulting from step c) for cells which are useful for the expression of a heterologous protein.

19. The method of claim 18 wherein the cells of human embryonic kidney origin are 293 cells.

20. The method of claim 18 wherein the cells of human embryonic kidney origin are 293S cells.

21. The cell line according to claim 16 designated 1G2 (ATCC deposit number PTA-87).

22. The method of claim 18 wherein i) the cells of step a) have a first desirable characteristic, ii) the cells of step b) have a second desirable characteristic, and iii) screening the cells in step d) provides cells which display at least one desirable characteristic of each of the cells of steps a) and b).

* * * * *